United States Patent
Chung et al.

(10) Patent No.: US 10,675,294 B2
(45) Date of Patent: Jun. 9, 2020

(54) PHARMACEUTICAL COMPOSITION CONTAINING 8 OXO-DEOXYGUANOSINE OR PHARMACEUTICALLY ACCEPTABLE SALT THEREOF AS ACTIVE INGREDIENT FOR TREATING CORNEAL DISEASE

(71) Applicants: GACHON UNIVERSITY OF INDUSTRY-ACADEMIC COOPERATION FOUNDATION, Gyeonggi-do (KR); GIL MEDICAL CENTER, Incheon (KR)

(72) Inventors: Myung-Hee Chung, Gyeonggi-do (KR); Dong Hyun Kim, Seoul (KR)

(73) Assignees: GACHON UNIVERSITY OF INDUSTRY-ACADEMIC COOPERATION FOUNDATION, Seongnam-si, Gyeonggi-Do (KR); GIL MEDICAL CENTER, Namdong-Gu, Incheon (KR)

( * ) Notice: Subject to any disclaimer, the term of this patent is extended or adjusted under 35 U.S.C. 154(b) by 0 days.

(21) Appl. No.: 16/376,140

(22) Filed: Apr. 5, 2019

(65) Prior Publication Data

US 2019/0282596 A1 Sep. 19, 2019

Related U.S. Application Data

(63) Continuation-in-part of application No. PCT/KR2017/011068, filed on Sep. 29, 2017.

(30) Foreign Application Priority Data

Oct. 6, 2016 (KR) .................. 10-2016-0128992

(51) Int. Cl.
| | |
|---|---|
| *A61K 31/708* | (2006.01) |
| *A61P 27/02* | (2006.01) |
| *A61K 9/00* | (2006.01) |
| *C11D 3/00* | (2006.01) |
| *C11D 3/28* | (2006.01) |
| *A61K 9/08* | (2006.01) |
| *A61K 31/522* | (2006.01) |
| *C11D 11/00* | (2006.01) |

(52) U.S. Cl.
CPC .......... *A61K 31/708* (2013.01); *A61K 9/0048* (2013.01); *A61K 9/08* (2013.01); *A61K 31/522* (2013.01); *A61P 27/02* (2018.01); *C11D 3/0078* (2013.01); *C11D 3/28* (2013.01); *C11D 11/0011* (2013.01)

(58) Field of Classification Search
CPC ...... A61K 31/708; A61K 9/0048; A61P 27/02
See application file for complete search history.

(56) References Cited

FOREIGN PATENT DOCUMENTS

| JP | 2012519652 A | 8/2013 |
|---|---|---|
| KR | 100793236 B1 | 1/2008 |
| KR | 1020100085697 A | 7/2010 |
| KR | 1020150036035 A | 4/2015 |

OTHER PUBLICATIONS

Google machine translation of patent KR20100085697A, https://patents.google.com/patent/KR20100085697A/en, accessed online on Feb. 24, 2020. (Year: 2020).*
Murano et al., Arch. Ophthalmol., 2008, 126 (6), p. 816-821. (Year: 2008).*
Panda, A. et al., "Topical autologous plate-let rich plasma eyedrops for acute corneal chemical injury," Cornea, 2012:31:989-993.
Dohlman, Ch et al., "Chemical burns to the eye:paradigm shifts in treatment," Corean, Jun. 2011:30(6):613-4.
Yi, K. et al., "Combined treatment with antioxidants and immunosuppressants on cytokine release by human peripheral blood mononuclear cells—chemically injured keratocyte reaction.," Mol Vis. 2011;17:2665-2671.
Onouchi, H. et al., 'Mitochondrial superoxide anion overproduction in Tet-mev-1 transgenic mice accelerates age-dependent corneal cell dysfunctions,' Investigative Ophthalmology & Visual Science, Aug. 31, 2012;53(9):5780-5787.
English Translation of PCT International Search Report dated Jan. 16, 2018 for related International Application No. PCT/KR2017/011068, 2 pgs.

* cited by examiner

Primary Examiner — Jonathan S Lau
(74) Attorney, Agent, or Firm — Fredrikson & Byron, P.A.

(57) ABSTRACT

The present invention relates to a pharmaceutical composition for treating corneal disease containing 8-oxo-deoxyguanosine (8-oxo-2'-deoxyguanosine) or a pharmaceutically acceptable salt thereof as an active ingredient. Specifically, by confirming that a corneal epithelium was restored (regenerated) quicker and the clarity of a cornea improved when it was administered W to a mouse model of corneal disease induced by ethanol, 8-oxo-deoxyguanosine (8-oxo-2'-deoxyguanosine) of the present invention may be useful for the treatment of corneal disease.

7 Claims, 15 Drawing Sheets

[Figure 1]
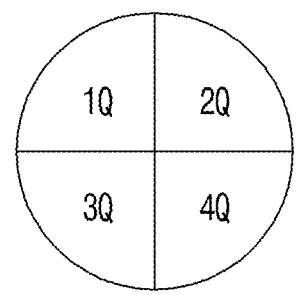

[Figure 2]
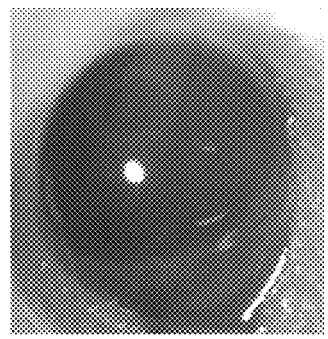
Normal group
day 0
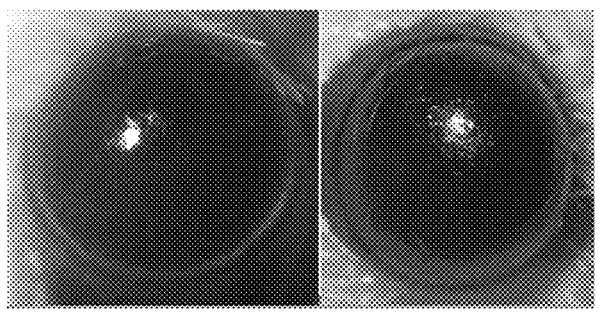
before staining ↓    after lysamine green staining ↓
Chemical damage
induced
by 100% ethanol

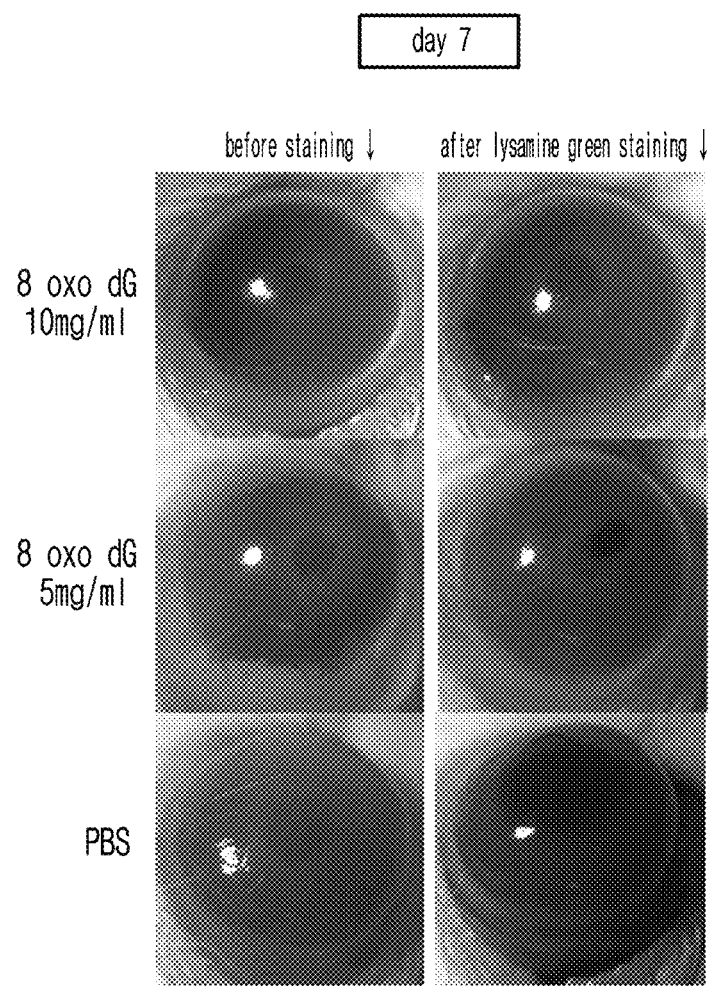
[Figure 3]

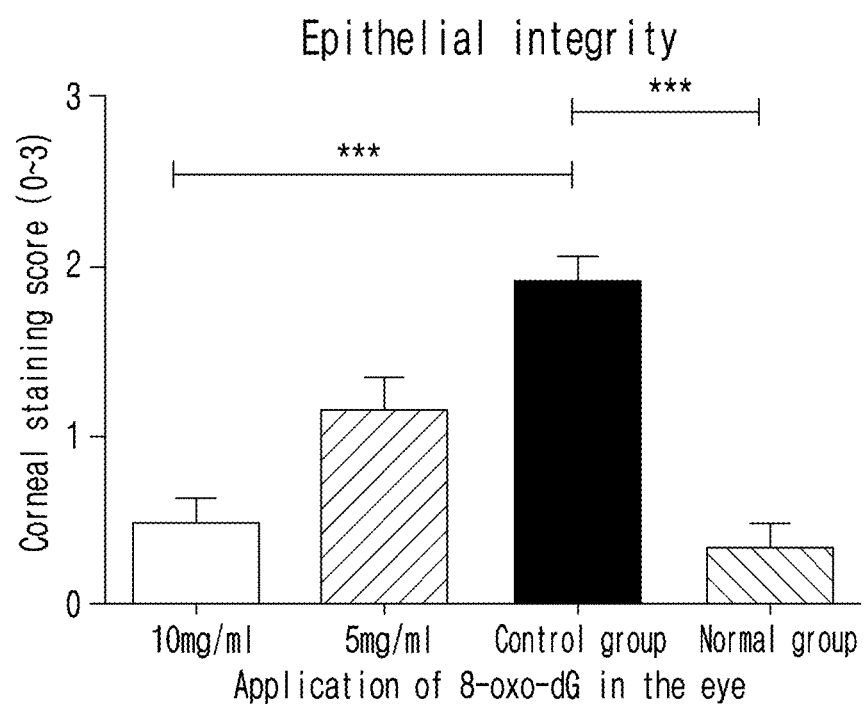
[Figure 4a]

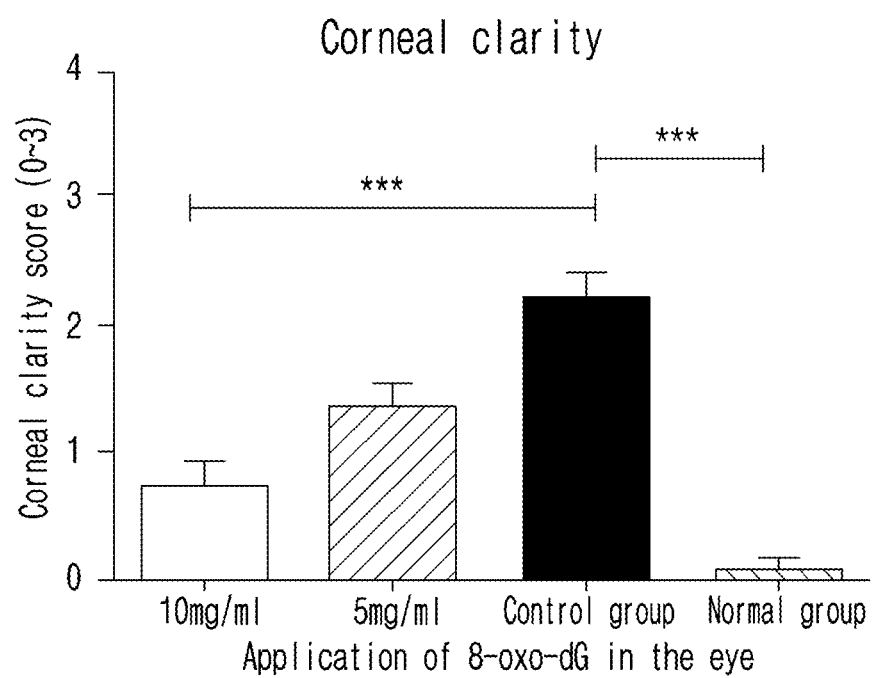
[Figure 4b]

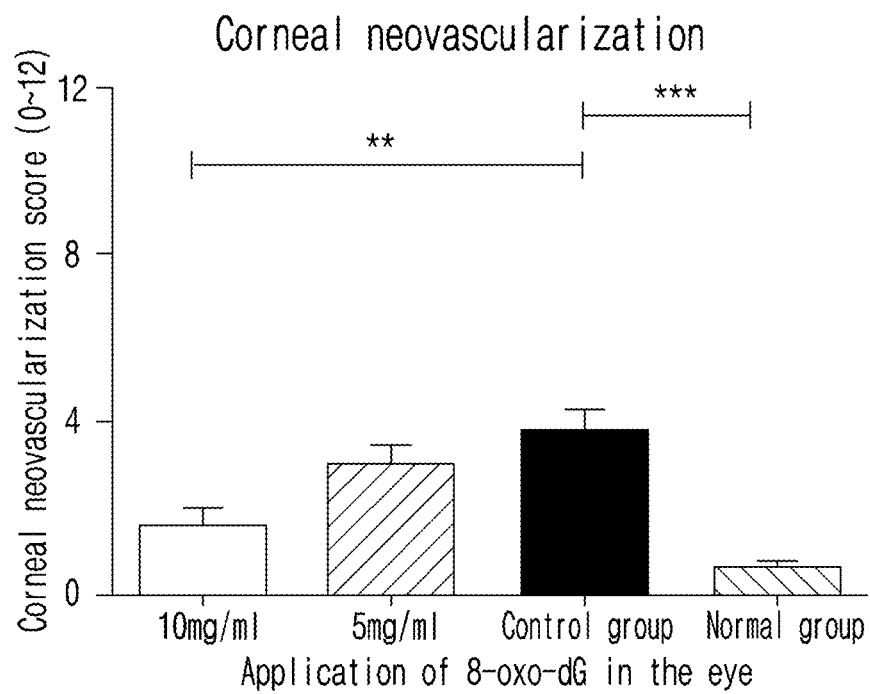
[Figure 4c]

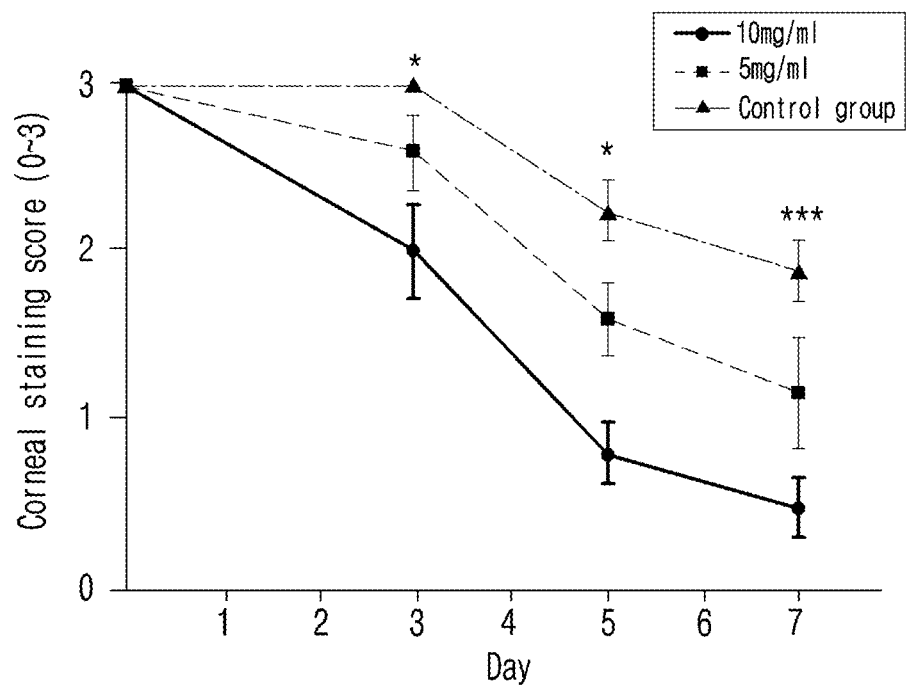
[Figure 4d]

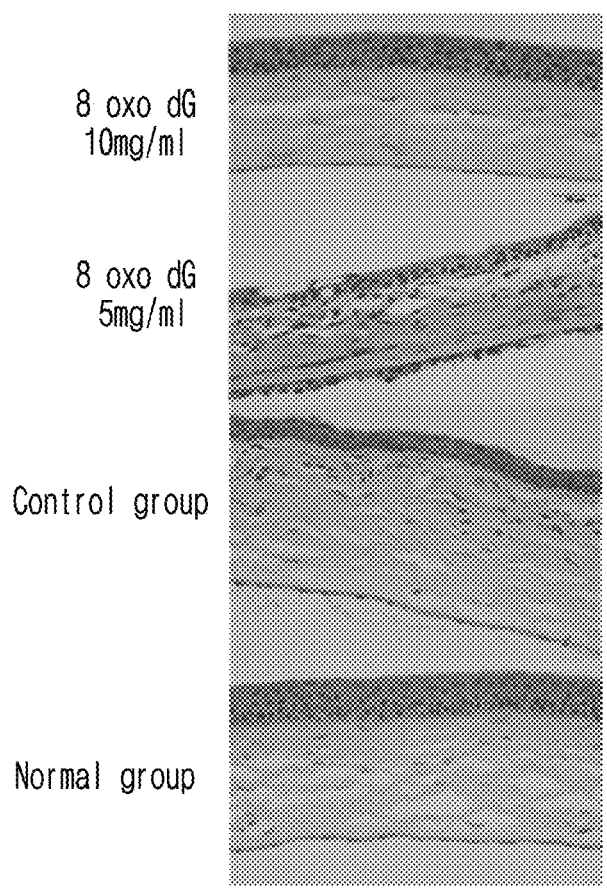
[Figure 5a]

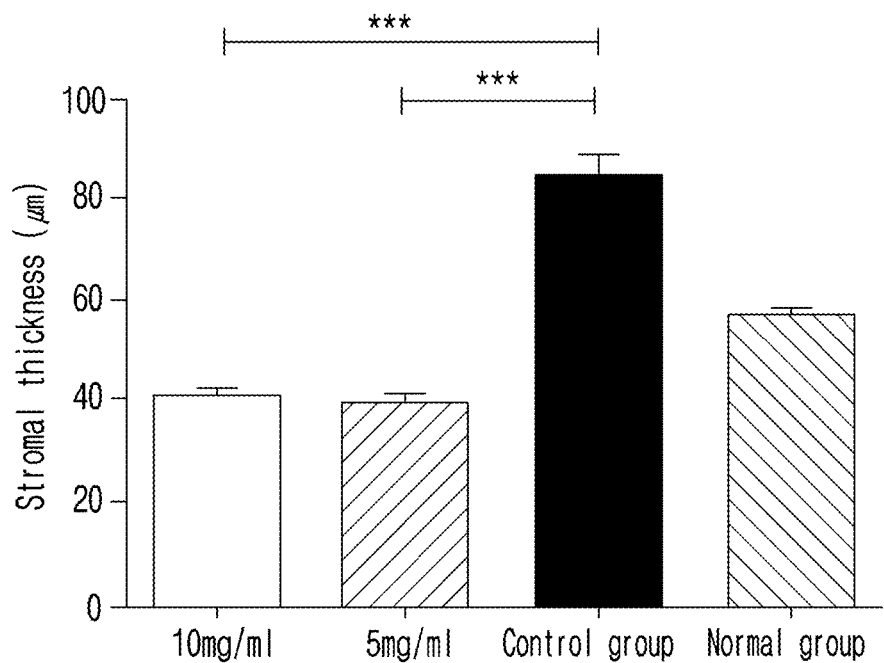
[Figure 5b]

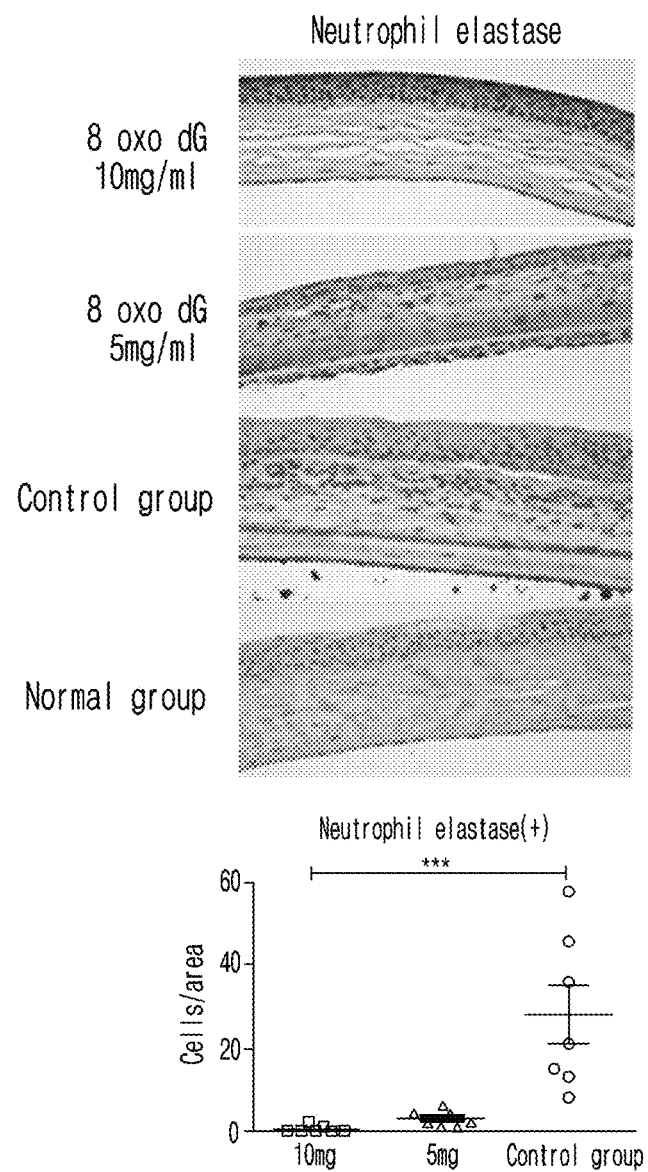
[Figure 6a]

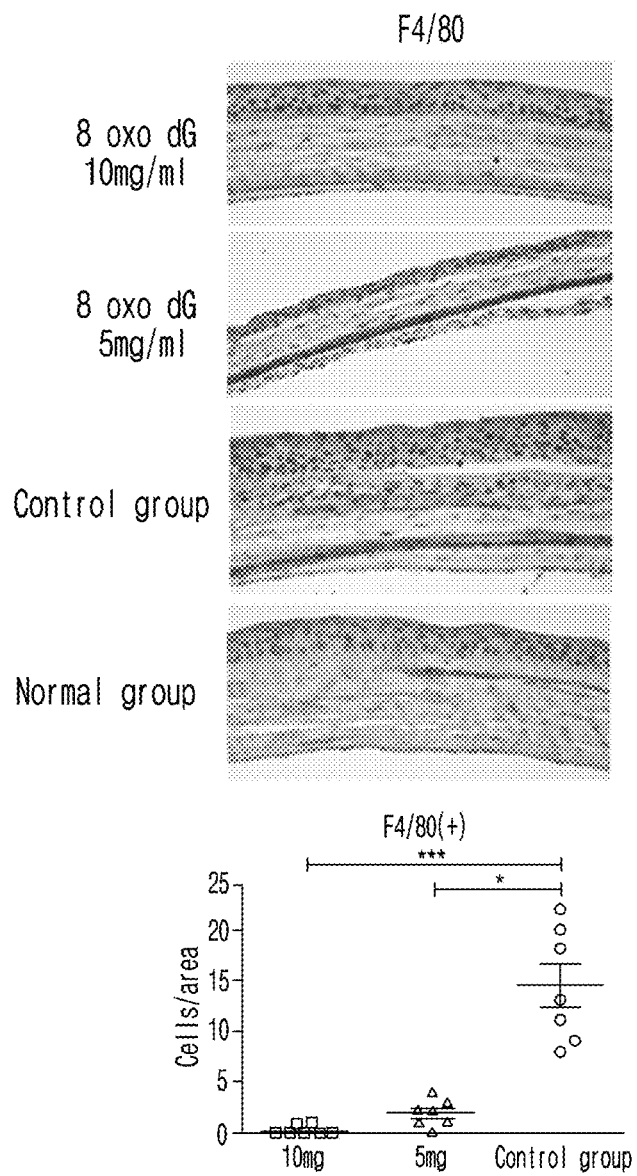

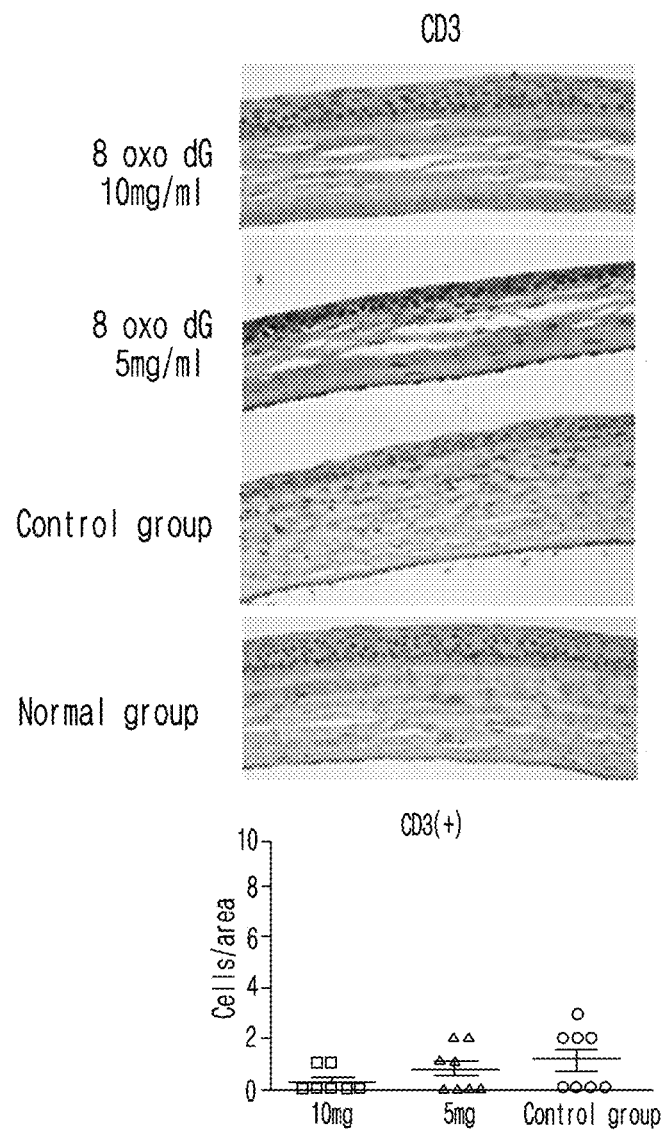

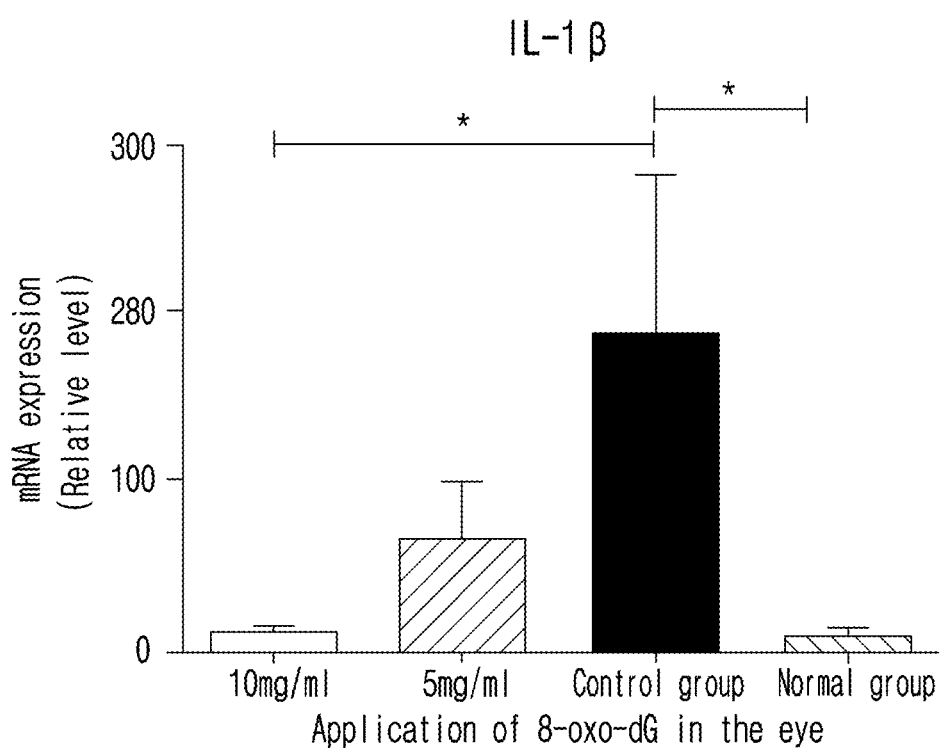
[Figure 7a]

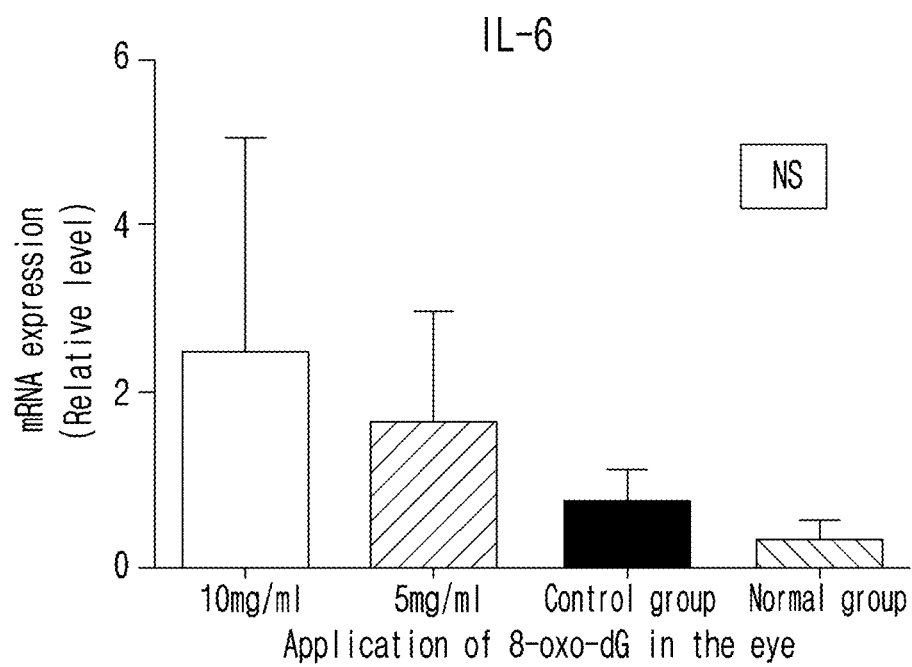
[Figure 7b]

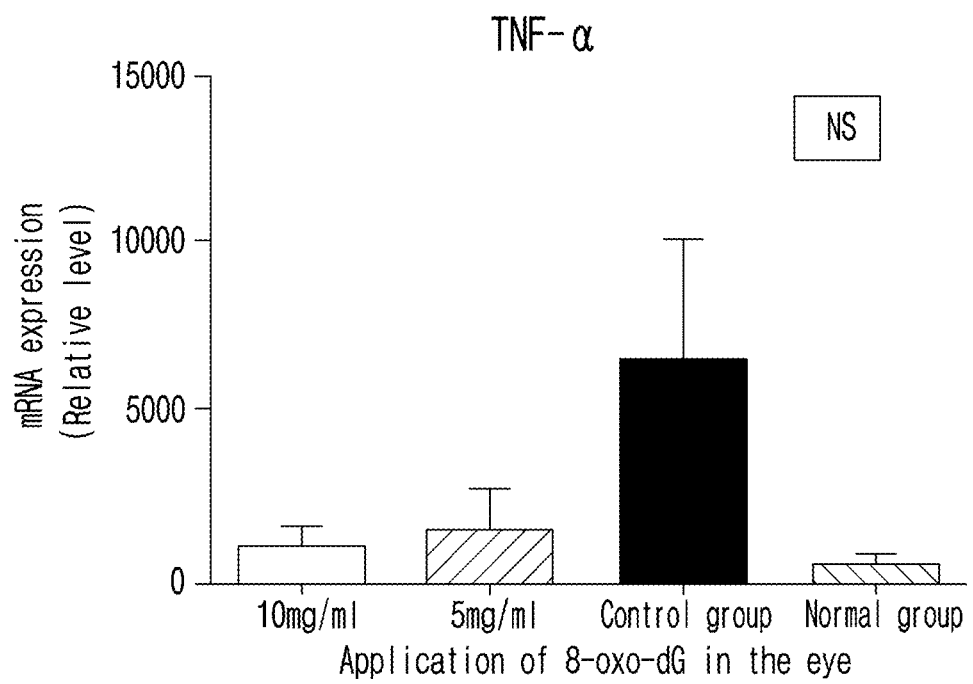

PHARMACEUTICAL COMPOSITION CONTAINING 8 OXO-DEOXYGUANOSINE OR PHARMACEUTICALLY ACCEPTABLE SALT THEREOF AS ACTIVE INGREDIENT FOR TREATING CORNEAL DISEASE

RELATED APPLICATIONS

This application is a continuation-in-part of International Application No. PCT/KR2017/011068, filed Sep. 29, 2017 and claims priority to Korean Application No. 10-2016-0128992, filed Oct. 6, 2016, the teachings of which are incorporated herein by reference.

BACKGROUND OF THE INVENTION

1. Field of the Invention

The present invention relates to a pharmaceutical composition comprising 8-oxo-2'-deoxyguanosine or a pharmaceutically acceptable salt thereof as an active ingredient for the treatment of corneal injury.

The present invention also relates to a method for preventing or treating corneal injury which comprises the step of administering the 8-oxo-2-deoxyguanosine compound or a pharmaceutically acceptable salt to a subject.

The present invention also relates to a use of a pharmaceutical composition comprising the 8-oxo-2-deoxyguanosine compound or a pharmaceutically acceptable salt thereof as an active ingredient for the prevention or treatment of corneal injury.

In addition, the present invention relates to a use of a composition comprising the 8-oxo-2-deoxyguanosine compound or a pharmaceutically acceptable salt thereof as an active ingredient for cleaning or preserving a contact lens or preserving an intraocular lens.

2. Description of the Related Art

The ocular surface is a special body surface consisted of conjunctival epithelial cells and corneal epithelial cells. These cells constitute a healthy ocular surface with tears secreted from the main lacrimal gland and the accessory lacrimal gland, and the healthy ocular surface is essential for the optimal function of the eyeballs.

The cornea is an organ taking one-sixth of the anterior ocular surface, which is transparent and has no blood vessels. The cornea not only protects the eyes from the outer environment but also plays an important role in light refraction and transmission. The nerve is well developed in the cornea. The cornea is consisted of the following five layers: corneal epithelium, Bowman's membrane, corneal stroma, Descemet's membrane and corneal endothelium. The corneal epithelial cells take about 10% of the thickness of the whole cornea, connect to the corneal epithelium, and are consisted of 5-7 layers. Basal cells of the bottom layer are proliferated and protrude outward and the cells are fallen out 7~14 days later.

One of the characteristics of the cornea, the avascular structure, must always remain transparent to preserve vision. However, the cornea is a thin tissue with a central thickness of 0.5 mm, so that it can be easily ruptured by a severe impact.

Corneal injury is caused by various reasons including trauma, infection, burn, surgery, autoimmune reaction, allergic hypersensitivity reaction, and contact lens.

When the cornea is injured, the cornea loses its ability to keep its clarity and accordingly it turns white. In addition, corneal burn causes wide-range tissue damage and decreased visual acuity, resulting in severe deterioration of quality of life. It is essential to control the inflammation in the early stage of corneal injury. In the late stage of corneal injury, opacity and neovascularization are observed on the cornea, which might cause not only ulcer and epileptic edema but also subsequent loss of visual acuity and induction of immune cell circulation leading to immune evasion and decrease of graft survival rate after corneal transplantation. In severe cases, they can lead to permanent visual loss.

The most difficult part in the clinical treatment of corneal injury is to control the inflammatory reaction caused by corneal injury. The inflammation caused by corneal injury increases reactive oxygen species (ROS) and inflammatory cascade reaction, which intervenes the recovery of the corneal epithelium so that pain continues and induces the synthesis of vascular endothelial growth factor (VEGF), basic fibroblast growth factor (bFGF) and matrix metalloproteinases (MMPs) so that it causes abnormality in the collagen structure of the corneal tissue and induces neovascularization, resulting in dense turbidity of the cornea.

As described hereinbefore, visual loss caused by corneal injury and subsequent inflammatory response is the most representative injury which concerns the whole world. Therefore, the development of an efficient and safe treating agent for corneal injury is highly requested.

Recently, several drugs including an immunosuppressant have been studied to discover their effect on neovascularization and opacity caused by corneal injury. (Panda A, Jain M, Vanathi M, et al. Topical autologous platelet-rich plasma eye drops for acute corneal chemical injury. Cornea. 2012; 31:989-993; Dohlman C H, Cade F, Pfister R. Chemical burns to the eye:paradigm shifts in treatment. Cornea. 2011; 30:613-614; Yi K, Chung T Y, Hyon J Y, et al. Combined treatment with antioxidants and immunosuppressants on cytokine release by human peripheral blood mononuclear cells—chemically injured keratocyte reaction. Mol Vis. 2011; 17:2665-2671). However, those clinically tested drugs are not so effective in preventing opacity and neovascularization in the cornea, yet.

In the meantime, 8-oxo-2'-deoxyguanosine (8-oxo-dG) is a material known to be released when DNA is damaged in vivo, and has been used as a biomarker for oxidative stress in various experiments related to atherosclerosis, diabetes and cancer, etc. According to the previous studies, exogenous 8-oxo-dG injected from the outside is not used for DNA synthesis, so that there is no chance of causing mutation and instead it has been confirmed in previous experiments with animal models having metabolic syndrome, gastritis and UV induced dermatitis that it inactivated Rac protein, the most representative GTPase related to biological signal transduction, so that such treatment effects as anti-inflammation and anti-oxidation were observed in those animal models. However, the use of the compound above for the treatment of corneal injury has not been examined, yet.

Thus, the present inventors tried to screen a material for inhibiting corneal injury induced inflammation as an effort to develop a novel substance for treating corneal injury. In the course of our study, the present inventors confirmed that 8-oxo-2'-deoxyguanosine was able to inhibit corneal injury induced inflammation and improve the recovery (regeneration) of corneal epithelium, suggesting that 8-oxo-2'-deoxyguanosine can be effectively used as a pharmaceutical composition for treating corneal injury, leading to the completion of the present invention.

SUMMARY OF THE INVENTION

It is an object of the present invention to provide a pharmaceutical composition comprising 8-oxo-2'-deoxyguanosine or a pharmaceutically acceptable salt thereof as an active ingredient for the treatment of corneal injury.

To achieve the above object, the present invention provides a pharmaceutical composition comprising the 8-oxo-2'-deoxyguanosine (8-oxo-dG) compound represented by formula 1 or a pharmaceutically acceptable salt thereof as an active ingredient for the prevention or treatment of corneal injury.

The present invention also provides an eye drop composition comprising the 8-oxo-2'-deoxyguanosine compound represented by formula 1 or a pharmaceutically acceptable salt thereof as an active ingredient for the prevention or treatment of corneal injury.

The present invention also provides a composition comprising the 8-oxo-2'-deoxyguanosine compound represented by formula 1 or a pharmaceutically acceptable salt thereof as an active ingredient for cleaning and preserving a contact lens.

The present invention also provides a composition comprising the 8-oxo-2'-deoxyguanosine compound represented by formula 1 or a pharmaceutically acceptable salt thereof as an active ingredient for preserving an intraocular lens.

The present invention also provides a pharmaceutical composition comprising the 8-oxo-2'-deoxyguanosine compound represented by formula 1 or a pharmaceutically acceptable salt thereof as an active ingredient for the prevention or treatment of one or more diseases selected from the group consisting of glaucoma, optic nerve disease, macular degeneration, retinal degeneration and retinal edema.

The present invention also provides a method for preventing or treating corneal injury comprising the step of administering the 8-oxo-2'-deoxyguanosine compound represented by formula 1 or a pharmaceutically acceptable salt thereof to a subject.

The present invention also provides a method for preventing or treating one or more diseases selected from the group consisting of glaucoma, optic nerve disease, macular degeneration, retinal degeneration and retinal edema, which comprises the step of administering the 8-oxo-2'-deoxyguanosine compound represented by formula 1 or a pharmaceutically acceptable salt thereof to a subject.

The present invention also provides a use of a pharmaceutical composition comprising the 8-oxo-2'-deoxyguanosine compound represented by formula 1 or a pharmaceutically acceptable salt thereof as an active ingredient for the prevention or treatment of corneal injury.

The present invention also provides a use of a pharmaceutical composition comprising the 8-oxo-2'-deoxyguanosine compound represented by formula 1 or a pharmaceutically acceptable salt thereof as an active ingredient for the prevention or treatment of one or more diseases selected from the group consisting of glaucoma, optic nerve disease, macular degeneration, retinal degeneration and retinal edema.

The present invention also provides a use of an eye drop composition comprising the 8-oxo-2'-deoxyguanosine compound represented by formula 1 or a pharmaceutically acceptable salt thereof as an active ingredient for the prevention or treatment of corneal injury.

The present invention also provides a use of a composition comprising the 8-oxo-2'-deoxyguanosine compound represented by formula 1 or a pharmaceutically acceptable salt thereof as an active ingredient for cleaning or preserving a contact lens.

In addition, the present invention provides a use of a composition comprising the 8-oxo-2'-deoxyguanosine compound represented by formula 1 or a pharmaceutically acceptable salt thereof as an active ingredient for preserving an intraocular lens.

Advantageous Effect

The pharmaceutical composition for treating corneal injury of the present invention comprising a 8-oxo-2'-deoxyguanosine compound or a pharmaceutically acceptable salt thereof as an active ingredient displays a better and quicker corneal epithelium restoration (regeneration) effect dose-dependently, compared with the control (phosphate buffered saline; PBS), in addition to the improvement of the clarity of a cornea in a mouse model of corneal injury induced by ethanol, indicating that the pharmaceutical composition of the present invention comprising a 8-oxo-2'-deoxyguanosine compound as an active ingredient can be effectively used for treating corneal injury.

BRIEF DESCRIPTION OF THE DRAWINGS

FIG. 1 is an illustrative diagram of the division of eyeballs in order to index and evaluate the degree of corneal neovascularization in stages FIG. 2 is a set of photographs illustrating the surface of the corneal epithelium of an ethanol induced corneal injury mouse model constructed by applying ethanol (100%) into the normal mouse eye after lysamine green staining.

FIG. 3 is a set of photographs illustrating the surface of the corneal epithelium of an ethanol induced corneal injury mouse model treated with 5 mg/ml or 10 mg/ml of 8-oxo-dG in the eye twice a day for a week, observed after lysamine green staining.

FIGS. 4a, 4b, 4c, and 4d are sets of graphs illustrating the time-dependent changes in the corneal epithelium tissue of an ethanol induced corneal injury mouse model treated with 8-oxo-dG in the eye twice a day for a week, wherein the changes were indexed and scored by the following items:

FIG. 4a: a graph showing the index scores of the epithelial integrity when 8-oxo-dG was applied in the eye at the concentration of 5 mg/ml or 10 mg/ml;

FIG. 4b: a graph showing the index scores of the corneal clarity when 8-oxo-dG was applied in the eye at the concentration of 5 mg/ml or 10 mg/ml;

FIG. 4c: a graph showing the index scores of the corneal neovascularization when 8-oxo-dG was applied in the eye at the concentration of 5 mg/ml or 10 mg/ml; and FIG. 4d: a graph showing the daily recovery of the corneal epithelium defects presented as corneal staining index scores when 8-oxo-dG was applied in the eye at the concentration of 5 mg/ml or 10 mg/ml.

FIGS. 5a and 5b are sets of photographs and a graph illustrating the corneal tissues of an ethanol induced corneal injury mouse model observed after the application of 8-oxo-dG into the eye for a week at the concentration of 5 mg/ml or 10 mg/ml:

FIG. 5a: a set of photographs showing the results of histological staining of the mouse corneal epithelium tissue; and FIG. 5b: a graph showing the thickness of the mouse corneal epithelium tissue.

FIGS. 6a, 6b, and 6c are sets of photographs and graphs illustrating the results of immunohistological staining of neutrophils, macrophages and T cells of an ethanol induced corneal injury mouse model treated with 8-oxo-dG in the eye for a week at the concentration of 5 mg/ml or 10 mg/ml and the number of inflammatory cells therein:

FIG. 6a: neutrophils;

FIG. 6b: macrophages; and

FIG. 6c: T cells.

FIGS. 7a, 7b and 7c are sets of graphs illustrating the expression of inflammatory cytokine mRNA in an ethanol induced corneal injury mouse model after the application of 8-oxo-dG in the eye for a week at the concentration of 5 mg/ml or 10 mg/ml:

FIG. 7a: expression of TNF-α mRNA;

FIG. 7b: expression of IL-1β mRNA; and

FIG. 7c: expression of IL-6 mRNA.

DESCRIPTION OF THE PREFERRED EMBODIMENTS

Hereinafter, the present invention is described in detail.

The present invention provides a pharmaceutical composition comprising the 8-oxo-2'-deoxyguanosine (8-oxo-dG) compound represented by formula 1 or a pharmaceutically acceptable salt thereof as an active ingredient for the prevention or treatment of corneal injury:

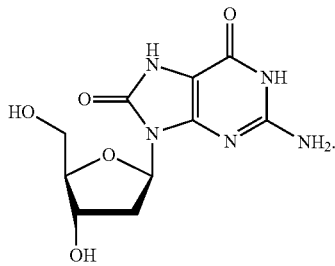

[Formula 1]

The present invention also provides a method for preventing or treating corneal injury comprising the step of administering the 8-oxo-2'-deoxyguanosine compound represented by formula 1 or a pharmaceutically acceptable salt thereof to a subject.

The present invention also provides a use of a pharmaceutical composition comprising the 8-oxo-2'-deoxyguanosine compound represented by formula 1 or a pharmaceutically acceptable salt thereof as an active ingredient for the prevention or treatment of corneal injury.

The said corneal injury is preferably caused by Stevenson-Johnson syndrome, Sjogren's syndrome, dry eye syndrome, trauma, orbital trauma caused by eye surgery (Eye surgery means all operations that involve the incision of the eye, which is exemplified by cataract surgery, glaucoma surgery, retinal surgery, LASIK surgery, and LASEK surgery, etc.), uveitis (infectious or noninfectious), immune rejection response after corneal transplantation and corneal/conjunctival epithelial disorder caused by an exogenous disease mediated by wearing a hard contact lens, but not always limited thereto.

The said corneal injury can also be induced preferably by a chemical, thermal damage or radiation, but not always limited thereto.

The chemical herein is preferably ethanol, but not always limited thereto.

In a preferred embodiment of the present invention, the 8-oxo-2'-deoxyguanosine (8-oxo-dG) compound of the present invention was instilled into the eye of an ethanol induced corneal injury mouse model twice a day for a week, followed by observation with the naked eye and photographs. As a result, the corneal epithelium surface defects induced by ethanol was significantly recovered by 8-oxo-dG dose-dependently over the time, compared with the control (PBS treated) and the clarity of the corneal tissue was also improved (see FIG. 3 and FIGS. 4a, 4b, 4c, and 4d). The corneal tissues of the ethanol induced corneal injury mouse model were stained, followed by direct observation. As a result, the corneal epithelium tissue which was damaged roughly and thickly by the existing corneal epithelium defects and the subsequent inflammation reaction was restored to normal condition by 8-oxo-dG (see FIGS. 5a and 5b).

Therefore, the composition comprising the 8-oxo-2'-deoxyguanosine (8-oxo-dG) compound of the present invention as an active ingredient can be effectively used as a composition for treating corneal injury, an eye drop composition for treating corneal injury, a composition for cleaning or preserving a contact lens, a composition for preserving an intraocular lens and a pharmaceutical composition for treating one or more diseases selected from the group consisting of glaucoma, optic nerve disease, macular degeneration, retinal degeneration and retinal edema.

The present invention includes not only the 8-oxo-2'-deoxyguanosine (8-oxo-dG) compound but also a pharmaceutically acceptable salt thereof, and a solvate, a hydrate, a racemate, or a stereoisomer possibly produced from the same.

The 8-oxo-2'-deoxyguanosine (8-oxo-dG) compound of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt of the present invention can be prepared by the conventional method. For example, the 8-oxo-2'-deoxyguanosine (8-oxo-dG) compound is dissolved in excessive acid aqueous solution and then the salt can be prepared by precipitation using a water-miscible organic solvent which is exemplified by methanol, ethanol, acetone, or acetonitrile.

It is also possible to prepare the acid addition salt by heating the above-mentioned compound and acid aqueous solution or alcohol, and then drying the mixture by evaporation, or suction-filtering the precipitated salt.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

When the composition of the present invention is formulated, it is prepared using diluents or excipients such as fillers, extenders, binders, wetting agents, disintegrating agents and surfactants.

Solid formulations for oral administration are tablets, pills, powders, granules, capsules and troches. These solid formulations are prepared by mixing the compound of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 81, cacao butter, laurin butter, glycerol, gelatin, etc.

The composition according to the present invention is administered in a pharmaceutically effective dose. The term "pharmaceutically effective dose" herein indicates the amount enough to treat the injury or disease with applicable, reasonable or risky concentration. The dose can be determined by considering many factors such as the type of injury or disease, severity of the injury or disease, activity of the drug, sensitivity to the drug, administration frequency and pathway, excretion, term of treatment, co-treatment drug and other factors regarded as relevant in the medicinal field.

The composition of the present invention can be administered as an individual therapeutic agent or in combination with other therapeutic agents, and can be administered sequentially or simultaneously with the conventional therapeutic agents, and can be administered singly or in multiple doses. It is important to take into account all of the above factors and to administer the amount in which the maximal effect can be obtained in a minimal amount without side effects, which can be easily determined by those in the art.

Particularly, the effective dose of the compound of the present invention is preferably 0.1 mg~100 mg/kg and more preferably 0.5 mg~10 mg/kg, which can be administered every day or every other day, or 1~3 times a day. However, the effective dose can be increased or decreased according to the administration pathway, severity of injury or disease, gender, body weight, and age of patient, etc, so that the effective dose above cannot limit the present invention in any aspects.

The composition of the present invention can be administered alone or treated together with surgical operation, hormone therapy, chemo-therapy and biological regulators.

The present invention also provides an eye drop composition comprising the 8-oxo-2'-deoxyguanosine compound represented by formula 1 or a pharmaceutically acceptable salt thereof as an active ingredient for the prevention or treatment of corneal injury.

The present invention also provides a use of an eye drop composition comprising the 8-oxo-2'-deoxyguanosine compound represented by formula 1 or a pharmaceutically acceptable salt thereof as an active ingredient for the prevention or treatment of corneal injury.

The composition comprising the 8-oxo-2'-deoxyguanosine compound or a pharmaceutically acceptable salt thereof as an active ingredient can be formulated as an eye drop composition by mixing with a proper carrier which is generally accepted in the pharmaceutical field. The eye drop composition herein is preferably an isotonic aqueous solution or a suspension. The composition above can be sterilized and/or contains adjuvants (ex: preservatives, stabilizers, wetting agents or salts/buffers for controlling osmotic pressure). The composition can also include other therapeutically usable substances.

An eye drop composition generally contains anionic polymers such as hyaluronic acid and carboxymethylcellulose or their pharmaceutically acceptable salts, which have been known to moisturize and lubricate in eye drops. The eye drop composition above can also contain a pharmaceutically acceptable carrier in addition to the above ingredients. The pharmaceutically acceptable carrier is exemplified by isotonic agents, buffers, stabilizers, pH regulators and solvents. The isotonic agent plays a role in regulating isotonicity of eye drops, which is exemplified by sodium chloride or potassium chloride. The buffer plays a role in regulating acidity or alkalinity of eye drops. The buffers generally used in the preparation of eye drops are exemplified by aminocaproic acid, sodium monohydrogen phosphate and sodium dihydrogen phosphate. The stabilizer plays a role in stabilizing eye drops, which is exemplified by sodium edetate and/or sodium perborate. The pH regulator adjusts pH of the eye drop composition, which is exemplified by hydrochloric acid and/or sodium hydroxide.

The solvent herein is preferably sterilized purified water or distilled water for injection. The eye drop composition of the present invention is preferably a liquid preparation. The eye drop composition above can additionally include preservatives and antiseptics, if necessary.

The preferable dose and application times of the eye drop composition of the present invention are 1-3 drops per application and 5-6 times a day, which can be appropriately increased or decreased according to the symptom. The dose for a particular subject can be controlled by weight, age, gender and health condition of a patient and period of application, application times and severity of injury, etc.

The present invention also provides a composition comprising the 8-oxo-2'-deoxyguanosine compound represented by formula 1 or a pharmaceutically acceptable salt thereof as an active ingredient for cleaning and preserving a contact lens.

The present invention also provides a use of a composition comprising the 8-oxo-2'-deoxyguanosine compound represented by formula 1 or a pharmaceutically acceptable salt thereof as an active ingredient for cleaning or preserving a contact lens.

The composition for cleaning a contact lens can contain a surfactant as a main component and the compound represented by formula (1) or a pharmaceutically acceptable salt thereof as an auxiliary component. The surfactant having a cleaning action not only includes anionic, cationic, nonionic and amphoteric surfactants but also various surfactants well informed to those in the field as a main cleaning agent. The composition can also include wetting agents, antibacterial agents, stabilizers, isotonizing agents, solubilizers, viscosity regulators or buffers.

The composition for preserving a contact lens can contain an aqueous solution for storing a contact lens such as saline, other buffers or deionized water in addition to the compound represented by formula (1) or a pharmaceutically acceptable salt thereof. Preferably, boric acid buffers such as boric acid and borax, acetic acid buffers such as acetic acid, sodium acetate and potassium acetate, phosphate buffers such as sodium hydrogen phosphate, sodium dihydrogen phosphate and potassium dihydrogen phosphate, carbonate buffers such as sodium carbonate and sodium hydrogen carbonate, citric acid buffers such as citric acid and sodium citrate, or trometamol buffers can be included in the composition. More preferably, the composition can contain salt-bearing brine comprising sodium chloride, sodium borate, sodium phosphate, sodium hydrogen phosphate, sodium dihydrogen phosphate or the corresponding potassium salt thereof. Wetting agents, surfactants, stabilizers, viscosity regulators, isotonizing agents, solubilizers, antioxidants, antiseptics, emulsifying agents, chelating agents or softening agents can be additionally included in the composition above.

The present invention also provides a composition comprising the 8-oxo-2'-deoxyguanosine compound represented by formula 1 or a pharmaceutically acceptable salt thereof as an active ingredient for preserving an intraocular lens.

The present invention also provides a use of a composition comprising the 8-oxo-2'-deoxyguanosine compound represented by formula 1 or a pharmaceutically acceptable salt thereof as an active ingredient for preserving an intraocular lens.

The intraocular lens is used to replace the original lens when the original lens has a disease—or is damaged. The intraocular lens is usually implanted into the eye to replace the original lens taken from the eye during cataract surgery. It is important to keep the intraocular lens free from contamination or infection until transplantation since it is used in the human body. The composition of the present invention demonstrates a therapeutic effect on ophthalmologic disease or ocular disease, so that it can be contained in an intraocular lens preserving solution to protect the intraocular lens from external infection or contamination and prevent endophthalmitis in the course of a transplantation process. The composition for preserving an intraocular lens of the present invention can additionally contain wetting agents, antibacterial agents, stabilizers, isotonizing agents, solubilizers, viscosity regulators, antioxidants or buffers The present invention also provides a pharmaceutical composition comprising the 8-oxo-2'-deoxyguanosine compound represented by formula 1 or a pharmaceutically acceptable salt thereof as an active ingredient for the prevention or treatment of one or more diseases selected from the group consisting of glaucoma, optic nerve disease, macular degeneration, retinal degeneration and retinal edema.

In addition, the present invention provides a method for preventing or treating one or more diseases selected from the group consisting of glaucoma, optic nerve disease, macular degeneration, retinal degeneration and retinal edema, which comprises the step of administering the 8-oxo-2'-deoxyguanosine compound represented by formula 1 or a pharmaceutically acceptable salt thereof to a subject.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Construction of Ethanol Induced Corneal Injury Mouse Model

To examine the therapeutic effect of 8-oxo-2'-deoxyguanosine (8-oxo-dG) on corneal injury, the present inventors constructed a corneal injurymouse model in advance.

Particularly, in order to construct a corneal injury mouse model using ethanol, a filter paper of 6 mm in diameter soaked in 100% ethanol was applied onto the cornea of the right eye of a female BALB/c mouse at 10 weeks of age for 30 seconds, followed by irrigation with PBS (phosphate-buffered saline) for 1 minute. In order to observe the defects of the corneal epithelium surface easily, the lysamine green reagent, which selectively stains the epithelium defect area, was treated on the surface of the damaged corneal epithelium and washed with physiological saline.

As a result, as shown in FIG. 2, it was confirmed that the corneal epithelium surface defect was induced after inducing corneal injury using ethanol, unlike the normal control, which was observed by the naked eye (before staining, FIG. 2). It was also confirmed after corneal staining that the defects were tough and overall on the corneal epithelium surface (after staining, FIG. 2).

Experimental Example 1: Therapeutic Effect of 8-Oxo-2'-Deoxyguanosine on Corneal Injury in Ethanol Induced Corneal Injury Mouse Model <1-1> Visual Confirmation of Corneal Epithelium Surface The 8-oxo-2'-deoxyguanosine (8-oxo-dG) compound used in this invention was purchased from Cambridge Isotope Laboratories (NLM-6715).

The 8-oxo-2'-deoxyguanosine compound prepared at the concentrations of 5 mg/ml and 10 mg/ml and the control PBS (phosphate-buffered saline) were applied into the eye of the ethanol induced corneal injury mouse model constructed in Example 1, respectively twice a day for a week, followed by observation with the naked eye and photographs (n=15 in each group).

As a result, as shown in FIG. 3, the corneal epithelium surface damage caused by ethanol was reduced by the treatment of 8-oxo-dG dose-dependently, compared with the control (PBS), which was confirmed by the naked eye (before staining, FIG. 3). It was also confirmed through lysamine green staining that the corneal epithelium surface damage was reduced significantly by the treatment of 8-oxo-dG dose-dependently, compared with the control (PBS) (after staining, FIG. 3).

<1-2> Confirmation of Recovery of Corneal Epithelium Damage with Clinical Index 8-oxo-dG was applied into the eye of the ethanol induced corneal injury mouse model for a week and then the recovery of the corneal epithelium damage was investigated. Particularly, the ethanol induced corneal injury mouse model examined in Experimental Example 1 was injected with Zoletil intramuscularly in order to anesthetize the mouse, followed by lysamine green staining on the cornea. Then, epithelial integrity and clarity of the corneal epithelium and corneal neovascularization were investigated and the results proceeded to clinical grading and scoring by items.

First, as shown in Table 1 below, the epithelial integrity was evaluated and scored by corneal staining (Choy E P et al. Curr Eye Res, 2004).

TABLE 1

| | Evaluation index (damage rate) of epithelial integrity |
|---|---|
| 0 | no epithelial defect |
| 1 | defect in epithelium ~¼ |
| 2 | defect in epithelium ~½ |
| 3 | defect in epithelium ~¾ |
| 4 | defect in epithelium ~¾ or more |

The corneal clarity was also evaluated and scored step by step. The indexes of the evaluation are as follows (Fantes et al, Arch Ophthalmol 1990).

TABLE 2

| | Corneal clarity index |
|---|---|
| 0 | Epithelial defect was not observed by the observation with slit-lamp. |
| 1 | Slight opacity was observed by the observation with direct or indirect lighting. |
| 2 | Soft fog patterns were easily observed by the observation with direct lighting. |
| 3 | Moderate opacity covered the iris partially. |
| 4 | Very dark opacity was observed over the whole eyeball. |

In addition, in order to evaluate and score the degree of corneal neovascularization, the cornea was divided into quadrants as shown in FIG. 1. Based on the limbus between the cornea and the sclera, 0.5 points were assigned to each part of the newly formed vessels in the inside, followed by indexing and scoring (total 12 scores) (Li et al, Molecular Vision 2010).

As a result, as shown in FIGS. 4a, 4b, 4c, and 4d, it was confirmed that the defect of the corneal epithelium surface induced by ethanol was reduced in the group treated with 8-oxo-dG dose-dependently, compared with the control group treated with PBS (FIG. 4a).

The corneal clarity scoring index was also reduced in the group treated with 8-oxo-dG dose-dependently, indicating that the corneal clarity was improved (FIG. 4b).

In addition, the neovascularization scoring index was reduced in the group treated with 8-oxo-dG to some degree (FIG. 4c).

During the application of 8-oxo-dG into the eye for a week, corneal staining was performed for a week to graphically identify the recovery of the corneal epithelial defects on daily basis. As a result, as shown in FIG. 4d, the defects on the corneal epithelium surface were significantly reduced in the group treated with 8-oxo-dG dose-dependently, indicating that the restoration (regeneration) was accelerated therein (FIG. 4d).

<1-3> Confirmation of Restoration of Corneal Injury by Histological Observation

The present inventors performed the following experiment to confirm the therapeutic effect of 8-oxo-dG on corneal injury by a histological observation method.

The ethanol induced corneal injury mouse model constructed in Example 1 was administered with 8-oxo-dG in the eye at the concentration of 5 mg/ml or 10 mg/ml and the control PBS (phosphate-buffered saline), twice a day for a week. The corneal tissues were extracted and fixed in 10% paraformaldehyde, followed by washing with PBS. The tissues were embedded in paraffin and the paraffin block was stained with H&E (haematoxylin and eosin), followed by direct observation under the microscope. The stromal thickness was measured by using Image J software.

As a result, as shown in FIGS. 5a and 5b, the corneal epithelium, which was damaged roughly and thickly by the corneal epithelium defects and the subsequent inflammation reaction, was restored to the normal level by the treatment of 8-oxo-dG (n=2).

<1-4> Confirmation of Restoration of Corneal Injury by Immunohistochemical Observation To investigate the therapeutic effect of 8-oxo-dG on corneal injury, the present inventors performed immunohistochemical staining with neutrophils, macrophages and T cells as follows.

Particularly, the ethanol induced corneal injury mouse model constructed in Example 1 was administered with 8-oxo-dG in the eye at the concentration of 5 mg/ml or 10 mg/ml and the control PBS (phosphate-buffered saline), twice a day for a week. The corneal tissues were extracted and fixed in 10% paraformaldehyde, followed by washing with PBS. The tissues were treated with anti-neutrophil elastase, anti CD3 and anti F4/80 antibodies (Abcam, Cambridge, UK), the markers of neutrophils, T lymphocytes and macrophages. After washing with PBS, the secondary antibody (REAL™ EnVision™ detection system, Dako) was applied thereto. The prepared slide was observed with an optical microscope at a magnification of 400 times. The immunostained cells in each section were counted by hand by two skilled examiners and the numbers were averaged.

As a result, as shown in FIGS. 6a, 6b and 6c, the number of the cells stained with anti-neutrophil elastase and anti F4/80 was reduced significantly in the group treated with 8-oxo-dG, compared with the control group. However, the number of the cells stained with anti CD3 was not much different among those groups. Therefore, it was confirmed that the infiltration of neutrophils and macrophages was significantly reduced in the group treated with 8-oxo-dG, compared with the control group.

<1-5> Inhibition of Inflammatory Cytokine Expression

The present inventors examined the expression of inflammatory cytokines by real time PCR as follows in order to confirm the therapeutic effect of 8-oxo-dG of the present invention on corneal injury.

Particularly, the ethanol induced corneal injury mouse model constructed in Example 1 was administered with 8-oxo-dG in the eye at the concentration of 5 mg/ml or 10 mg/ml and the control PBS (phosphate-buffered saline), twice a day for a week. The corneal tissue was extracted and homogenized with a sonicator (Ultrasonic Processor, Cole Parmer Instruments, Vernon Hills, Ill., USA). Then, corneal RNA was extracted by using RNeasy Mini kit (Qiagen, Valencia, Calif., USA). CDNA was synthesized with the same amount of RNA of each corneal sample and real-time PCR (ABI 7500 Real Time PCR System, Applied Biosystems, Carlsbad, Calif., USA) was performed. Taqman Gene Expression Assays were used for real-time PCR. The detailed inflammatory cytokines were as follows. IL-1β (Taqman Gene Expression Assays ID, Mm00434228_m1), IL-6 (Taqman Gene Expression Assays ID, Mm00446190_m1), and IFN-α (Taqman Gene Expression Assays ID, Mm01168134_m1).

As a result, as shown in FIGS. 7a, 7b and 7c, the expression of IL-1β, the representative inflammatory cytokine, was significantly reduced in the group treated with 10 mg/ml of 8-oxo-dG, compared with the control group. The expression of another representative inflammatory cytokine TNF-α was not significantly but slightly reduced in the group treated with 8-oxo-dG, compared with the control group. The expression of IL-6 was not much different among those three groups.

Hereinafter, the Manufacturing Examples for the pharmaceutical composition of the present invention are described, but the present invention is not limited thereto.

Manufacturing Example 1: Preparation of Injectable Solutions

Injectable solutions were prepared by mixing 3.5 mg of 8-oxo-dG, 3.0 mg of sodium metabisulfite, 0.8 mg of methylparaben, 0.1 mg of propylparaben and an appropriate amount of sterilized distilled water for injection, putting the mixture into 2 ml, ampoules and sterilizing thereof by the conventional method for preparing injectable solutions.

Manufacturing Example 2: Preparation of Tablets

Tablets were prepared by mixing 3.5 mg of 8-oxo-dG, 100 mg of lactose, 100 mg of starch and an appropriate amount of magnesium stearate by the conventional method for preparing tablets.

Manufacturing Example 3: Preparation of Capsules

Capsules were prepared by mixing 3.5 mg of 8-oxo-dG, 50 mg of lactose, 50 mg of starch, 2 mg of talc and an appropriate amount of magnesium stearate, which filled gelatin capsules according to the conventional method for preparing capsules.

What is claimed is:

1. A method for preventing or treating corneal injury comprising the step of administering to a subject the 8-oxo-2'-deoxyguanosine compound represented by the following formula 1 or a pharmaceutically acceptable salt thereof as an active ingredient:

[Formula 1]

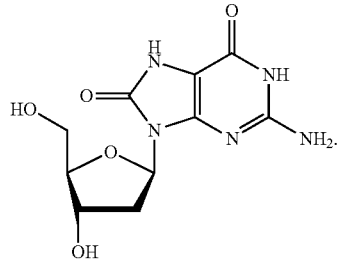

2. The method for preventing or treating corneal injury according to claim 1, wherein the corneal injury is caused by Stevenson-Johnson syndrome, Sjogren's syndrome, dry eye syndrome, trauma, orbital trauma caused by eye surgery, uveitis (infectious or noninfectious), immune rejection response after corneal transplantation or corneal/conjunctival epithelial disorder caused by an exogenous disease mediated by wearing a hard contact lens.

3. The method for preventing or treating corneal injury according to claim 1, wherein the corneal injury is caused by a chemical, thermal damage or radiation.

4. The method for preventing or treating corneal injury according to claim 3, wherein the chemical is ethanol.

5. The method for preventing or treating corneal injury according to claim 1, wherein the administration is performed using eye drops.

6. A method for cleaning or preserving a contact lens comprising the step of treating the contact lens with the 8-oxo-2'-deoxyguanosine compound represented by the following formula 1 or a pharmaceutically acceptable salt thereof as an active ingredient:

[Formula 1]

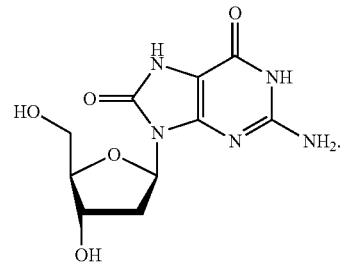

7. A method for preserving an intraocular lens comprising the step of treating the intraocular lens with the 8-oxo-2'-deoxyguanosine compound represented by the following formula 1 or a pharmaceutically acceptable salt thereof as an active ingredient:

[Formula 1]

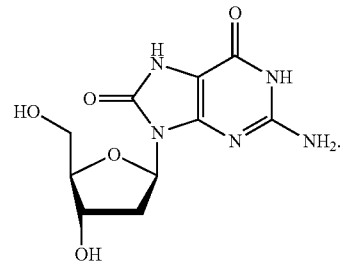

* * * * *